United States Patent [19]

Dornauer et al.

[11] 3,939,159

[45] Feb. 17, 1976

[54] SPIRO(PYRROLO (1,2-A)QUINOXALINES)

[75] Inventors: Horst Dornauer, Kelkheim, Germany; Vernon Brian Anderson, High Bridge, N.J.

[73] Assignee: American Hoechst Corporation, Bridgewater, N.J.

[22] Filed: May 29, 1974

[21] Appl. No.: 474,447

[52] U.S. Cl. 260/250 Q; 260/326.5 R; 260/326.5 L; 260/326.9; 424/250
[51] Int. Cl.$^2$.............. C07D 207/32; C07D 487/20
[58] Field of Search.................. 260/250 Q, 250 QN

[56] References Cited
OTHER PUBLICATIONS

Cheeseman et al., Chem. Abstracts, Vol. 75, Abstract No. 98537 b, (1971).

Grantham et al., Chem. Abstracts, Vol. 69, Abstract No. 43889 p, (1968).

*Primary Examiner*—Alton D. Rollins
*Attorney, Agent, or Firm*—Curtis, Morris & Safford

[57] ABSTRACT

Spiro[pyrrolo(1,2-a)quinoxalines] and their physiologically tolerable acid addition salts possessing anticonvulsant and central nervous system depressant properties, and a process for their preparation are described.

8 Claims, No Drawings

SPIRO(PYRROLO (1,2-A)QUINOXALINES)

This invention relates to spiro[pyrrolo(1,2-a)-quinoxalines] and their physiologically tolerable acid addition salts possessing anticonvulsant and central nervous system depressant properties, and to a process for their preparation.

To the best of our knowledge, the compounds of this invention have not heretofore been described. Pyrrolo-[1,2-a]quinoxaline derivatives are mentioned in Indian Journal of Chemistry, Vol. 10, 1972, pp. 344–350 and pyrrolo-[1,2-a]quinoxalines and pyrrolo[1,2-a]benzodiazepines are mentioned in an article by G. W. H. Cheeseman and M. Rafiq [J. Chem. Soc. (c), 1971, pp. 2732-2734].

The compounds of the invention have the formula:

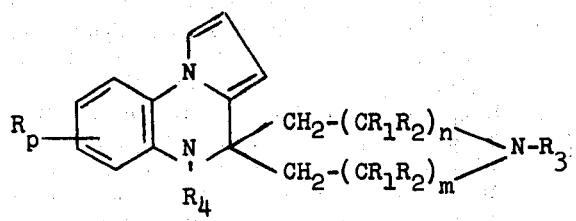

in which R is alkyl of from 1 to 4 carbon atoms, alkoxy of from 1 to 4 carbon atoms or halogen; $m$, $n$ and $p$ are integers from 0 to 2; $R_1$ and $R_2$ are hydrogen or methyl; $R_3$ is hydrogen, alkyl of from 1 to 4 carbon atoms, alkanoyl of 2 to 6 carbon atoms, cycloalkylcarbonyl of from 4 to 6 carbon atoms or phenalkyl of from 7 to 9 carbon atoms; and $R_4$ is hydrogen atom or alkanoyl of from 2 to 3 carbon atoms; and the physiologically tolerable acid addition salts thereof.

The compounds of the invention can be prepared by a multi-step sequence of reactions. In the first step, a 2-nitroaniline is reacted with 2,5-dimethoxytetrahydrofuran in the presence or absence of a suitable solvent and with an acid catalyst to provide the corresponding 1-(2-nitrophenyl)pyrrole in accordance with the reaction:

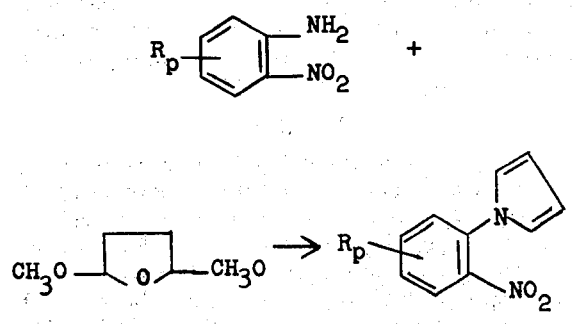

in which R and $p$ are as defined above. A preferred method is to reflux the reagents in glacial acetic acid for a few minutes to 1 hour.

The 1-(2-nitrophenyl)pyrrole is reduced by methods known to the art to produce the corresponding 1-(2-aminophenyl)pyrrole. One preferred method is to add sodium dithionite to a solution of the 1-(2-nitrophenyl)pyrrole in water and tetrahydrofuran. Another preferred method is to hydrogenate the 1-(2-nitrophenyl)pyrrole in 95% ethanol with a palladium on charcoal catalyst. The resulting 1-(2-aminophenyl)pyrrole is then reacted with a cycloazalkanone in the presence or absence of a suitable solvent with an acid catalyst to produce the corresponding compound of the invention in accordance with the following equation:

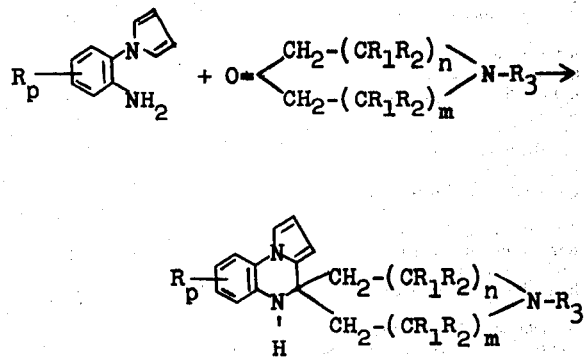

in which $n$, $m$, $p$, R, $R_1$, $R_2$ and $R_3$ are as defined earlier.

When $R_3$ represents benzyl, the resulting compounds can be hydrogenated by methods known to the art, such as by reacting the compound with concentrated hydrochloric acid in 95% ethanol and in the presence of a palladium catalyst, thereby to replace the benzyl with hydrogen.

When $R_3$ is hydrogen the compounds can be acylated by reacting with a alkanoyl halide or cycloalkylcarbonyl halide in a suitable solvent, at a temperature of about 5°C., in the presence of triethylamine to replace the $R_3$ hydrogen with an alkanoyl or cycloalkylcarbonyl group.

The compounds can also be acylated with a suitable alkyl acid derivative in a suitable solvent to give compounds of the formula:

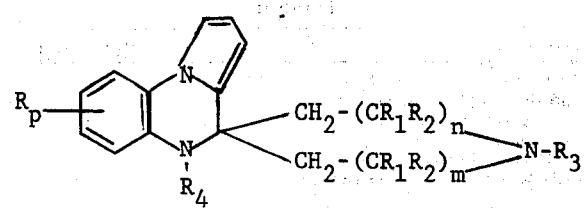

in which $R_4$ is an alkanoyl of from 2 to 3 carbon atoms. In a preferred procedure the acid derivative is an anhydride and the reaction medium is refluxing toluene.

The compounds of the invention are useful as anticonvulsant agents as illustrated by the methods of Bastian et al. (J. W. Bastian, W. E. Drause, S. A. Ridlon, and N. Ercoli, J. Pharmacol. Exptl. Therap., 127, 75 (1959), and Swinyard et al. (H. A. Swinyard, W. C. Brown, and L. S. Goodman, ibid., 106, 319 (1952). Male COBS mice are challenged with metrazol and electroshock and the minimum effective intraperitoneal dose (MED) in the metrazol test, and the intraperitoneal dose protecting 50% of the mice ($PD_{50}$) against the extensor tonic phase induced by electroshock are shown in Table I for some of the compounds of the invention.

Table I

| Compound | Metrazol MED., mg/kg | Electroshock PD$_{50}$, mg/kg |
|---|---|---|
| 4,5-Dihydro-1'-methylspiro-[pyrrolo(1,2-a)quinoxaline-4,4'-piperidine] | 5 | 24 |
| 4,5-Dihydro-7-chloro-1'-methylspiro[pyrrolo(1,2-a)-quinoxaline-4,4'-piperidine]-hydrochloride | 25 | 20 |
| 7,8-Dichloro-4,5-dihydro-1'-methylspiro[pyrrolo(1,2-a)-quinoxaline-4,4'-piperidine] | 25 | 64 |
| 4,5-Dihydro-2',2',6',6'-tetramethylspiro[pyrrolo-(1,2-a)quinoxaline-4,4'-piperidine]hydroiodide | 25 | 17 |
| 4,5-Dihydro-1',7-dimethyl-spiro[pyrrolo(1,2-a)quinoxaline-4,4'-piperidine]hydrochloride | — | 16 |
| 4,5-Dihydro-7-methoxy-1'-methyl-spiro[pyrrolo(1,2-a)quinoxaline-4,4'-piperidine] | — | 55 |
| 4,5-Dihydro-7-methyl-1'-benzyl spiro[pyrrolo(1,2-a)quinoxaline-4,4'-piperidine]hydrochloride | — | 84 |

The compounds of the invention are also useful as depressant agents on the central nervous system. These tranquilizing effects are measured according to the mouse observation procedure of S. Irwin, Psychopharmacologia, 9, 259 (1966). In this test, male COBS mice are dosed intraperitoneally with the drug and its effects on behavior and reflex depression together with muscle relaxation are determined by the degree of deviation from control scores. The overall result for 3 animals in each category for some compounds of this invention is expressed in terms of the minimum effective dose (MED) and is illustrated in Table II.

Table II

| Compound | MED. mg/kg. |
|---|---|
| 4,5-Dihydro-1'-(2-phenethyl)-spiro[pyrrolo(1,2-a)quinoxaline-4-4'-piperidine] | 40 |
| 4,5-Dihydro-1'-methylspiro[pyrrolo-(1,2-a)quinoxaline-4,4-piperidine] | 50 |
| 4,5-Dihydro-2',2',6',6'-tetramethyl-spiro[pyrrolo(1,2-a)quinoxaline-4,4'-piperidine]hydroiodide | 50 |
| 4,5-Dihydro-5-acetyl-1'-(2-phenethyl)-spiro[pyrrolo(1,2-a)quinoxaline-4,4'-piperidine]hydrochloride | 50 |
| 4,5-Dihydrospiro[pyrrolo(1,2-a)quinoxaline-4,4'-piperidine]hydrochloride | 50 |
| 4,5-Dihydro-7-chloro-1'-methylspiro-[pyrrolo(1,2-a)quinoxaline-4,4'-piperidine]hydrochloride | 50 |

The compounds of the present invention may be administered to a patient by any convenient route such as orally, intramuscularly, intravenously, subcutaneously or intraperitoneally. The preferred route of administration is oral, for example, with an inert diluent or with an edible carrier or in gelatin capsules or tablets.

For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of the active compound, but may be varied depending upon the particular form and may conveniently be between 7% to about 70% of the unit by weight. The amount of active compound in such compositions is such that a suitable dosage will be obtained. Preferred compositions and preparations according to the present invention are prepared so that an oral dosage unit form contains between 1–200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions may be pharmaceutically pure and nontoxic in the amounts utilized.

The compounds of this invention may also be intraveneously administered as sterile aqueous solutions. The pH of these solutions may be adjusted with phosphate or citrate buffers, and the solutions may contain perservatives. The solution should contain at least 0.5% of active compound and may conveniently contain from 1–10% of active compound. The concentration will be such that a suitable dosage will be obtained.

Acids useful for preparing the physiologically tolerable acid addition salts of the invention include inorganic acids such as hydrochloric, hydrobromic, sulfuric, nitric, phosphoric and perchloric acids, as well as organic acids such as tartaric, citric, acetic, succinic, maleic and ethane disulfonic acids.

EXAMPLE 1 a. 136.0 g (1.0 mole) of 2,5-dimethoxytetrahydrofuran are added dropwise to a stirred solution of 140.8 g of o-nitroaniline in 700 ml. of glacial acetic acid. The reaction mixture is heated under reflux for 1½ hours. The glacial acetic acid is evaporated to leave a brown oil. The oil is distilled and dissolved in benzene. The benzene solution is extracted with 5% hydrochloric acid and saturated sodium chloride solution. The benzene solution is dried with anhydrous sodium sulfate, filtered and concentrated, giving (2-nitrophenyl)pyrrole as an orange oil.

b. A solution of 50.7 g (0.27 mole) of 1-(2-nitrophenyl)pyrrole in 200 ml. of 95% ethanol is placed into a Parr hydrogenation bottle, 2.0 g of (5%) Pd/C is added, hydrogen is introduced, and the bottle is shaken. The ethanol solution is filtered and the solvent is removed to give crystals, m.p. 95°–97°C., of 1-(2-aminophenyl)-pyrrole.

c. 7.47 g (0.066 mole) of 1-methyl-4-piperidone and 4 ml. of glacial acetic acid are added to a solution of 9.50 g (0.06 mole) of 1-(2-aminophenyl)pyrrole in 150 ml. of absolute ethanol. The mixture is refluxed for 6 hours and concentrated to dryness, and the residue is treated with slightly alkaline water. The resulting precipitate is filtered, dried, and recrystallized from ethanol to give crystals, m.p. 138°–140°C., of 4,5-dihydro-1′-methylspiro[pyrrolo(1,2-a)quinoxaline-4,4′-piperidine].

Analysis: Calculated for $C_{16}H_{19}N_3$: 75.85% C; 7.56% H; 16.59% N. Found: 76.06% C; 7.68% H; 16.87% N.

EXAMPLE 2

6.62 g (0.035 mole) of 1-benzyl-4-piperidone and 2 ml. of glacial acetic acid under nitrogen are added to a solution of 5.0 g (0.032 mole) of 1-(2-aminophenyl)pyrrole [Example 1(b)] in 80 ml. of absolute ethanol. By the manipulative procedure described in Example 1(c), a solid is obtained. The solid is recrystallized from isopropanol to give light orange crystals, m.p. 132°–133°C., of 1′-benzyl -4,5-dihydrospiro[pyrrolo(1,2-a)quinoxaline-4,4′-piperidine].

Analysis: Calculated for $C_{22}H_{23}N_3$: 80.24% C; 6.99% H. Found: 80.02% C; 7.17% H.

EXAMPLE 3

12.46 g (0.044 mole) of 2,2,6,6-tetramethyl-4-piperidone hydroiodide and 3 ml. of glacial acetic acid are added to a solution of 6.33 g (0.04 mole) of 1-(2-aminophenyl)pyrrole [Example 1(b)] in 150 ml. of absolute ethanol. The solution is refluxed for 6 hours and the precipitate is filtered, dried, and recrystallized from methanol to give crystals, m.p. 261°–262°C., of 4,5-dihydro-2′,2′,6′,6′-tetramethylspiro[pyrrolo(1,2-a)quinoxaline-4,4′-piperidine]hydroiodide.

Analysis: Calculated for $C_{19}H_{26}IN_3$: 53.90% C; 6.19% H; 9.92% N. Found: 53.60% C; 6.19% H; 9.81% N.

EXAMPLE 4

A solution of 6.33 g (0.04 mole) of 1-(2-aminophenyl)pyrrole [Example 1(b)], 6.21 g (0.04 mole) of N-acetyl-4-piperidone and 3 ml. of glacial acetic acid in 150 ml. of absolute ethanol is treated by the manipulative procedure described above in Example 3 to give crystals, m.p. 177°–178°C., of 1′-acetyl-4,5-dihydrospiro[pyrrolo(1,2-a)-quinoxaline-4,4′-piperidine].

Analysis: Calculated for $C_{17}H_{19}N_3O$: 72.57% C; 6.81% H; 14.94% N. Found: 72.81% C; 6.93% H; 15.22% N.

EXAMPLE 5

6.83 g (0.044 mole) of 1-butyl-4-piperidone and 3 ml. of glacial acetic acid are added to a solution of 6.33 g (0.04 mole) of 1-(2-aminophenyl)pyrrole in 100 ml. of absolute ethanol. The solution is refluxed for 6 hours. The solvent is removed leaving a yellow residue. The residue is covered with a solution of $Na_2CO_3$ in water and kept overnight in a refrigerator. The compound solidifies, is filtered, dried, and recrystallized from ethanol to give crystals, m.p. 59°–60°C., of 1′-n-butyl-4,5-dihydrospiro-[pyrrolo(1,2-a)quinoxaline-4,4′-piperidine].

Analysis: Calculated for $C_{19}H_{25}N_3$: 77.25% C; 8.53% H; 14.22% N. Found: 76.83% C; 8.67% H; 14.07% N.

EXAMPLE 6

Following the manipulative procedure described in Example 5, substituting 1-(2-phenylethyl)-4-piperidone for 1-butyl-4-piperidone, produces crystals, m.p. 121°–123°C., of 4,5-dihydro-1′-(2-phenylethyl)spiro[pyrrolo(1,2-a)quinoxaline-4,4′-piperidine].

Analysis: Calculated for $C_{23}H_{25}N_3$: 80.43% C; 7.34% H; 12.23% N. Found: 80.42% C; 7.46% H; 12.29% N.

EXAMPLE 7

9.02 g (0.04 mole) of 1-benzyl-3-piperidone hydrochloride and 5 ml. of glacial acetic acid are added to a solution of 6.32 g (0.04 mole) of 1-(2-aminophenyl)pyrrole in 150 ml. of absolute ethanol. The solution is refluxed for 12 hours. The reaction mixture is cooled to ambient temperature, the precipitate is filtered off, dried, and recrystallized from ethanol to give crystals, m.p. 255°–256°C., of 4,5-dihydro-1′-benzylspiro[pyrrolo(1,2-a)quinoxaline-4,3′-piperidine]hydrochloride.

Analysis: Calculated for $C_{22}H_{24}ClN_3$: 72.21% C; 6.61% H; 11.48% N. Found: 71.84% C; 6.67% H; 11.57% N.

EXAMPLE 8

0.7 g of 10% Pd/C are added to a suspension of 5.49g (0.015 mole) of 1′-benzyl-4,5-dihydrospiro(1,2-a)-[quinoxaline-4,3′-piperidine]hydrochloride in 150 ml. of 95% ethanol. The mixture is shaken in a hydrogen atmosphere until the calculated amount of hydrogen is consumed. The reaction mixture is filtered while hot, the filtrate evaporated to dryness, and the residue is recrystallized from ethanol to give crystals, m.p. 300°–302°C., of 4,5-dihydrospiro[pyrrolo(1,2-a)quinoxaline-4,3′-piperidine] hydrochloride.

Analysis: Calculated for $C_{15}H_{18}ClN_3$: 65.33% C; 6.58% H; 15.24% N. Found: 65.25% C; 6.61% H; 15.41% N.

EXAMPLE 9

A suspension of 14.81 g (0.045 mole) of 1′-benzyl-4,5-dihydrospiro[pyrrole(1,2-a)quinoxaline-4,4′-piperidine] (Example 2), 3.72 ml. of concentrated hydrochloric acid and 150 ml. of 95% ethanol is placed into a Parr hydrogenation bottle. 2.04 g of 10% Pd/C are added to the suspension. The mixture is hydrogenated at 50°C. for 48 hours. The reaction solution is filtered and the solvent is removed to leave an oil. The oil is chromatographed on silica gel with methanol in benzene to provide a pink solid. The solid is recrystallized twice from absolute ethanol giving crystals, m.p. 292°–294°C., of 4,5-dihydrospiro[pyrrolo(1,2-a)quinoxaline-4,4′-piperidine]hydrochloride.

Analysis: Calculated for $C_{15}H_{18}ClN_3$: 65.36% C; 6.53% H; 15.23% N. Found: 65.15% C; 6.75% H; 14.94% N.

EXAMPLE 10

3.7 g (0.037 mole) of triethylamine are added to a stirred cold solution of 7.0 g (0.03 mole) of 4,5-dihydrospiro[pyrrolo(1,2-a)quinoxaline-4,4′-piperidine] free base of Example 9 in 75 ml. of chloroform. A solution of 3.03 g (0.03 mole) of cyclopropylcarbonyl chloride in 76 ml. of chloroform is added dropwise into the solution, the ice bath removed, and the solution is stirred for 3 hours. The solution is washed with water, dried, and filtered; and the solvent is removed, leaving a brown oil. The oil is chromatographed on silica gel with chloroform and methanol mixtures to give a solid which is recrystallized from isopropanol to give white crystals, m.p. 199°–200°C., of 1'-cyclopropylcarbonyl-4,5-dihydrospiro[pyrrolo(1,2-a)quinoxaline-4,4'-piperidine].

Analysis: Calculated for $C_{19}H_{21}N_3O$: 74.27% C; 6.84% H; 13.68% N. Found: 73.65% C; 6.93% H; 13.59% N.

EXAMPLE 11

A solution of 3.0 g (0.0087 mole) of 4,5-dihydro-1'-(2-phenethyl)spiro[pyrrolo(1,2-a)quinoxaline -4,4'-piperidine] (Example 6) and 1.02 g (0.01 mole) of acetic anhydride in toluene is refluxed for 14 hours. The mixture is concentrated and the resulting oil is dissolved in ether and treated with ethereal-hydrogen chloride. A white solid precipitates, and is filtered, dried, and recrystallized from ethylacetate to give crystals, m.p. 191°–194°C. of 5-acetyl-4, 5-dihydro-1'-(2-phenethyl)spiro[pyrrolo)1,2-a)quinoxaline-4,4'-piperidine]hydrochloride.

Analysis: Calculated for $C_{25}H_{28}ClN_3O$: 71.16% C; 6.69% H; 9.96% N. Found: 70.85% C; 6.69% H; 10.05% N.

EXAMPLE 12

Following the manipulative procedure of Example 11, 5.07 g (0.02 mole) of 4,5-dihydro-1''-methylspiro[pyrrolo(1,2-a)quinoxaline-4,4'-piperidine] (Example 1) and 2.05 g (0.02 mole) of acetic anhydride are reacted to give a white precipitate. The precipitate is recrystallized from ethanol to give 4,5-dihydro-5-acetyl-1'-methylspiro[pyrrolo(1,2-a)quinoxaline-4,4'-piperidine] hydrochloride, m.p. 239°–240°C. dec.

Analysis: Calculated for $C_{18}H_{22}ClN_3O$: 65.15% C; 6.68% H; 12.66% N. Found: 65.41% C; 6.77% H; 12.76% N.

EXAMPLE 13 a. 100 g (0.75 mole) of 2,5-dimethoxytetrahydrofuran are added dropwise to a stirred solution of 86.3 g (0.5 mole) of 4-chloro-2-nitroaniline in 500 ml. of glacial acetic acid. The solution is refluxed under a nitrogen atmosphere for 30 minutes, filtered, and poured into 2500 ml. of water. The aqueous solution is extracted with chloroform. The chloroform solution is dried with anhydrous sodium sulfate and concentrated to a brown oil. The brown oil is dissolved in an ether-petroleum ether-mixture and placed in a refrigerator overnight. An orange solid precipitates and is recrystallized from an ether petroleum ether mixture to give 1-(4-chloro-2-nitrophenyl) pyrrole, m.p. 55°–56°C.

b. 10 g of sodium hydrosulfite are added portionwise to a stirred solution of 10.0 g (0.045 mole) of 1-(4-chloro-2-nitrophenyl)pyrrole, 200 ml. of tetrahydrofuran and 100 ml. of water, and the solution is heated on a steam bath for 5 minutes. An additional 10 g of sodium hydrosulfite are added and the solution is again heated on a steam bath for 5 minutes. Then 23 g more of sodium hydrosulfite and a solution of 200 ml. of ethanol in 250 ml. of water are added and heated for 5 minutes on a steam bath. The organic solvents are distilled, leaving a suspension of a tan solid. The solid is filtered, washed with water, dried, and recrystallized from hexane to give yellow needles, m.p. 89°–90°C. of 1-(2-amino-4-chlorophenyl)pyrrole.

c. A solution of 5.0 g (0.026 mole) of 1-(2-amino-4-chlorophenyl)pyrrole, 80 ml. of absolute ethanol, 3.95 g (0.028 mole) of 1-acetyl-4-piperidone and 2 ml. of glacial acetic acid is refluxed for 29 hours. The solvent is removed, leaving a yellow oil. The oil is crystallized from absolute ethanol producing white crystals, m.p. 219°–220°C. of 1'-acetyl-7-chloro-4,5-dihydrospiro[pyrrolo(1,2-a)quinoxaline-4,4'-piperidine].

Analysis: Calculated for $C_{17}H_{18}ClN_3O$: 64.66% C; 5.71% H; 11.25% Cl; 13.31% N. Found: 64.42% C; 5.65% H; 11.17% Cl; 13.35% N.

EXAMPLE 14

1.7 g (0.016 mole) of 1-methyl-4-piperidone and 3 ml. of glacial acetic acid are added to a solution of 2.7 g (0.014 mole) of 1-(2-amino-4-chloro-phenyl) pyrrole, Example 13(b), in 50 ml. of absolute ethanol. The solution is refluxed for 36 hours and concentrated, and the residue dissolved in water. The aqueous solution is filtered, and the filtrate is basified. A solid precipitates, is filtered, and dried. The solid is dissolved in ether and ethereal-hydrogen chloride is added. The resulting precipitate is filtered, dried, and recrystallized from methanol to give 7-chloro-4,5-dihydro-1'-methylspiro-[pyrrolo (1,2-a)quinoxaline-4,4'-piperidine] hydrochloride, m.p. 297°–298°C.

Analysis: Calculated for $C_{16}H_{19}Cl_2N_3$: 59.26% C; 5.90% H; 12.96% N. Found: 58.85% C; 5.94% H; 12.80% N.

EXAMPLE 15

5.29 g (0.028 mole) of 1-benzyl-4-piperidone and 2 ml. of glacial acetic acid are added to a solution of 5.0 g (0.026 mole) of 1-(2-amino-4-chlorophenyl)pyrrole [Example 13(b)] in 80 ml. of absolute ethanol. The solution is refluxed, leaving a yellow oil. The oil is washed with a potassium hydroxide solution, then water, and placed in a refrigerator overnight. The tan solid which forms is dissolved in ether, and ethereal hydrogen chloride is added. The resulting precipitate is washed with water and dried to give 1'-benzyl-7-chloro-4,5-dihydrospiro[pyrrolo(1,2-a)quinoxaline-4,4'-piperidine]hydrochloride, m.p. 282°–283°C.

Analysis: Calculated for $C_{22}H_{23}Cl_2N_3$: 66.00% C; 5.75% H; 10.50% N. Found: 65.85% C; 5.93% H; 10.43% N.

EXAMPLE 16 a. Following the manipulative procedure described in Example 13(a), the reaction of 76.0 g (0.5 mole) of 4-methyl-2-nitroaniline, and 100.0 g (0.75 mole) of 2,5-dimethoxytetrahydrofuran produces yellow-red crystals, m.p. 57°–58°C., of 1-(4-methyl-2-nitrophenyl)pyrrole.

b. 20 g of sodium hydrosulfite are added portionwise to a solution of 18.18 g (0.09 mole) of 1-(4-methyl-2-nitrophenyl)pyrrole in 400 ml. of tetrahydrofuran and 200 ml. of water. The resulting solution is heated on a steam bath for 5 minutes and an additional 20 g. of sodium hydrosulfite are added and the solution is heated for 5 minutes on a steam bath. Then 38.3 g. of sodium hydrosulfite and a solution of 400 ml. of ethanol and 500 ml. of water are added, and again the solution is heated on a steam bath for 5 minutes. The solvent is removed to give a tan solid which is recrystallized from hexane to give white crystals, m.p. 89°–90°C. of 1-(2-amino-4-methylphenyl)pyrrole.

c. 1.70 g (0.015 mole) of 1-methyl-4-piperidone and 3 ml. of glacial acetic acid are added to a solution of 2.58 g (0.015 mole) of 1-(2-amino-4-methyl-phenyl)- pyrrole in 50 ml. of absolute ethanol. The solution is refluxed for 10 hours and concentrated, and the residue is dissolved in water and basified. A white solid precipitates and is filtered and dried. The precipitate is dissolved in ether, ethereal hydrogen chloride is added, and the resulting precipitate is filtered and dried. The hydrochloride salt is recrystallized from ethanol to give 4,5-dihydro-1',7-dimethylspiro[pyrrolo(1,2-a)quinoxaline-4,4'-piperidine]hydrochloride, m.p. 302°–304°C.

Analysis: Calculated for $C_{17}H_{22}ClN_3$: 67.20% C; 7.30% H; 13.83% N. Found: 67.13% C; 7.42% H; 14.01% N.

EXAMPLE 17

4.73 g (0.025 mole) of 1-benzyl-4-piperidone and 2 ml. of glacial acetic acid are added to a solution of 50 g (0.025 mole) of 1-(2-amino-4-methylphenyl) pyrrole [Example 16(b)] in 80 ml. of absolute ethanol. The solution is refluxed under nitrogen with stirring for 24 hours. The solvent is removed, leaving a tan oil. The oil is placed under water and cooled for 24 hours to produce a semi-solid. The semi-solid is dissolved in ether and ethereal-hydrogen chloride is added to produce the hydrochloride salt. The salt is recrystallized from absolute ethanol to give 1'-benzyl-4,5-dihydro-7-methylspiro[pyrrolo(1,2-a)quinoxaline-4,4'-piperidine]hydrochloride, m.p. 276°–277°C.

Analysis: Calculated for $C_{23}H_{26}ClN_3$: 72.73% C; 6.85% H; 9.35% N. Found: 72.76% C; 7.01% H; 9.33% N.

EXAMPLE 18

8.46 g (0.06 mole) of 1-acetyl-4-piperidone and 3 ml. of glacial acetic acid are added to a solution of 12.0 g (0.06 mole) of 1-(2-amino-4-methyl-phenyl)pyrrole [Example 16(b)] in 160 ml. of absolute ethanol. The solution is refluxed under nitrogen with stirring for 24 hours and cooled. A solid precipitates and is filtered. The solid is recrystallized from absolute ethanol to give white crystals, m.p. 212°–213°C. of 1'-acetyl-4,5-dihydro-7-methylspiro[pyrrolo(1,2-a)quinoxaline-4,4'-piperidine].

Analysis: Calculated for $C_{18}H_{21}N_3O$: 73.22% C; 7.12% H; 14.24% N. Found: 72.96% C; 7.12% H; 14.42% N.

EXAMPLE 19 a. 100 g (0.75 mole) of 2,5-dimethoxytetrahydrofuran are added to a solution of 84.1 g (0.5 mole) of 4-methoxy-2-nitroaniline in 500 ml. of glacial acetic acid. The solution is refluxed for 30 minutes, poured into 2500 ml. of water, and neutralized with potassium hydroxide. A solid precipitates and is filtered, dried, and recrystallized from ether to give 1-(4-methoxy-2-nitrophenyl)pyrrole, m.p. 75.5°–76.5°C.

b. A stirred solution of 33.5 g (0.154 mole) of 1-(4-methoxy-2-nitrophenyl)pyrrole in 684 ml. of tetrahydrofuran and 340 ml. of water is treated according to the manipulative procedure described in Example 13(b) to give 1-(2-amino-4-methoxyphenyl)pyrrole, m.p. 42°–43°C.

c. 3.48 g (0.03 mole) of 1-methyl-4-piperidone and 3 ml. of glacial acetic acid are added to a solution of 5.65 g (0.03 mole) of 1-(2-amino-4-methoxy-phenyl) pyrrole in 100 ml. of absolute ethanol. The solution is refluxed for 15 hours and concentrated, and the residue is dissolved in water. The solution is filtered and basified. A solid precipitates and is filtered, dried and recrystallized from ethanol to give 4,5-dihydro-7-methoxy-1'-methylspiro[pyrrolo(1,2-a)quinoxaline-4,4'-piperidine], m.p. 124°–125°C.

Analysis: Calculated for $C_{17}H_{21}N_3O$: 72.05% C; 7.47% H; 14.83% N. Found: 72.19% C; 7.43% H; 14.90% N.

EXAMPLE 20

7.06 g (0.05 mole) of 1-acetyl-4-piperidone and 5 ml. of glacial acetic acid are added to a solution of 9.41 g (0.05 mole) of 1-(2-amino-4-methoxy-phenyl)pyrrole [Example 19(b)] in 150 ml. of absolute ethanol. The solution is refluxed for 12 hours. The volume of the solvent is reduced to about one fifth and the solution is cooled. A solid precipitates and is filtered, dried, and recrystallized from ethanol to give 1'-acetyl-4,5-dihydro-7-methoxyspiro[pyrrolo(1,2-a) quinoxaline-4,4'-piperidine], m.p. 211°–213°C.

Analysis: Calculated for $C_{18}H_{21}N_3O_2$: 69.43% C; 6.80% H; 13.50% N. Found: 69.20% C; 6.80% H; 13.67% N.

EXAMPLE 21

510 g (0.027 mole) of 1-benzyl-4-piperidone and 2 ml. of glacial acetic acid are added to a solution of 50 g (0.027 mole) of 1-(2-amino-4-methoxy-phenyl)pyrrole [Example 19(b)] in 80 ml. of absolute ethanol. The solution is refluxed for 43 hours and concentrated to an oil which is washed with water. The oil is recrystallized from isopropanol to give 1'-benzyl-7-methoxy-4,5-dihydrospiro[pyrrolo(1,2-a)quinoxaline-4,4'-piperidine], m.p. 123°–124°C.

Analysis: Calculated for $C_{23}H_{25}N_3O$: 76.88% C; 6.96% H; 11.70% N. Found: 76.81% C; 7.03% H; 11.73% N.

EXAMPLE 22 a. Following the manipulative procedure described in Example 19(a), 100.0 g (0.48 mole) of 4,5-dichloro-2-nitroanline and 100 g (0.75 mole) of 2,5-dimethoxytetrahydrofuran produces 1-(4,5-dichloro-2-nitrophenyl) pyrrole. This is recrystallized from petroleum ether to give crystals, m.p. 69.5°–70.5°C.

b. A stirred solution of 42.4 g (0.165 mole) of 1-(4,5-dichloro-2-nitrophenyl)pyrrole in 730 ml. of tetrahydrofuran and 365 ml. of water is treated according to the manipulative procedure described above in Example 13(b) to give 1-(2-amino-4,5-dichlorophenyl)pyrrole, m.p. 57°–58°C.

c. 3.39 g (0.03 mole) of 1-methyl-4-piperidone and 5 ml. of glacial acetic acid are added to a solution of 6.81 g (0.03 mole) of 1-(2-amino-4,5-dichlorophenyl)pyrrole in 100 ml. of absolute ethanol. The solution is refluxed for 50 hours and concentrated, and the residue is dissolved in water. The solution is filtered and basified. A solid precipitates and is filtered, dried, and recrystallized from ethanol to give 7,8-dichloro-4,5-dihydro-1'-methylspiro[pyrrolo(1,2-a)quinoxaline-4,4'-piperidine], m.p. 214°–215°C.

Analysis: Calculated for $C_{16}H_{17}Cl_2N_3$: 59.63% C; 5.32% H; 13.04% N. Found: 59.40% C; 5.28% H; 12.93% N.

EXAMPLE 23

7.06 g (0.05 mole) of 1-acetyl-4-piperidone and 5 ml. of glacial acetic acid are added to a solution of 11.36 g (0.05 mole) of 1-(2-amino-4,5-dichlorophenyl) pyrrole [Example 22(b)] in 150 ml. of absolute ethanol. The solution is refluxed for 45 hours. The volume of the solution is reduced by one fifth and cooled. A solid precipitates and is filtered, dried, and recrystallized from methanol to give 1'-acetyl-7,8-dichloro-4,5-dihydrospiro [pyrrolo(1,2-a)quinoxaline)4,4'-piperidine], m.p. 171°–173°C. dec.

Analysis: Calculated for $C_{17}H_{17}Cl_2N_3O$: 58.29% C; 4.89% H; 11.99; % N. Found: 57.57% C; 5.04% H; 11.76% N.

EXAMPLE 24

3.78 g (0.02 mole) of 1-benzyl-4-piperidone and 2 ml. of glacial acetic acid are added to a solution of 5.0 g (0.02 mole) of 1-(2-amino-4,5-dichlorophenyl)pyrrole in 80 ml. of absolute ethanol. The solution is refluxed for 67 hours. The solvent is removed and the resulting oil is triturated with isopropanol to give a solid. The solid is recrystallized from 75 ml. of isopropanol to give 1'-benzyl-7,8-dichloro-4,5-dihydrospiro[pyrrolo(1,2-a)quinoxaline-4,4'-piperiddidne] m.p. 151°–152°C.

Analysis: Calculated for $C_{22}H_{21}Cl_2N_3$: 66.36% C; 5.28% H; 10.55% N. 17.84% Cl Found: 66.28% C; 5.36% H; 10.53% N. 18.07% Cl

Other compounds of the invention prepared in a similar manner include 1'-butyl-4,5-dihydrospiro[pyrrolo(1,2-a)quinoxaline-4,4'-hexamethyleneimine] and 5-acetyl-4,5-dihydro-1'-(phenethyl)spiro[pyrrolo(1,2-a)quinoxaline-4,5'-heptamethyleneimine].

We claim:

1. A compound of the formula:

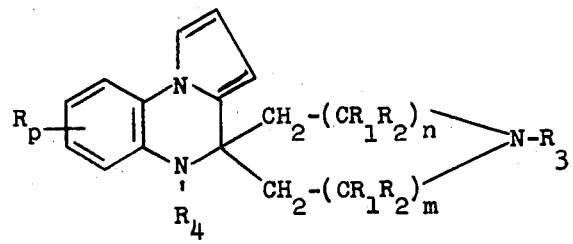

in which R is alkyl or from 1 to 3 carbon atoms, alkoxy of from 1 to 2 carbon atoms or halogen; $m$, $n$ and $p$ are integers from 0 to 2, the sum of $m$ and $n$ being from 2 to 4; $R_1$ and $R_2$ are hydrogen or methyl; $R_3$ is hydrogen, alkyl of from 1 to 4 carbon atoms, alkanoyl of from 2 to 6 carbon atoms, cycloalkylcarbonyl of from 4 to 6 carbon atoms or aralkyl of from 7 to 9 carbon atoms; and $R_4$ is hydrogen or alkanoyl of from 2 to 3 carbon atoms; and the physiologically tolerable acid addition salts thereof.

2. The compound defined in claim 1 which is 4,5-dihydro-1'-methylspiro[pyrrolo(1,2-a)quinoxaline-4,4'-piperidine] and the physiologically tolerable acid addition salts thereof.

3. The compound defined in claim 1 which is 7-chloro-4,5-dihydro-1'-methylspiro[pyrrolo(1,2-a)quinoxaline-4,4'-piperidine], and the physiologically tolerable acid addition salts thereof.

4. The compound defined in claim 1 which is 7, 8-dichloro-4,5-dihydro-1'-methylspiro[pyrrolo(1,2-a)quinoxaline-4,4'-piperidine] and the physiologically tolerable acid addition salts thereof.

5. The compound defined in claim 1 which is 4,5-dihydro-2',2',6',6'-tetramethylspiro[pyrrolo(1,2-a)quinoxaline-4,4'-piperidine] and the physiologically tolerable acid addition salts thereof.

6. The compound defined in claim 1 which is 4,5-dihydro-1',7-dimethylspiro[pyrrolo(1,2-a)quinoxaline-4,4'-piperidine] and the physiologically tolerable acid addition salts thereof.

7. The compound defined in claim 1 which is 4,5-dihydro-1'-(2-phenethyl)spiro[pyrrolo(1,2-a)quinoxaline-4,4'-piperidine] and the physiologically tolerable acid addition salts thereof.

8. The compound defined in claim 1 which is 5-acetyl-4,5-dihydro-1'-(2-phenethyl)spiro[pyrrolo(1,2-a)quinoxaline-4,4'-piperidine] and the physiologically tolerable acid addition salts thereof.

* * * * *